United States Patent [19]

Harandi et al.

[11] Patent Number: 5,154,801
[45] Date of Patent: Oct. 13, 1992

[54] ADVANCES IN PRODUCT SEPARATION IN DIPE PROCESS

[75] Inventors: Mohsen N. Harandi, Lawrenceville; Hartley Owen, Belle Mead; Frank P. Ragonese, Cherry Hill; James A. Stoos, Blackwood, all of N.J.

[73] Assignee: Mobil Oil Corporation, Fairfax, Va.

[21] Appl. No.: 527,973

[22] Filed: May 24, 1990

[51] Int. Cl.$^5$ .............................. B01D 41/06
[52] U.S. Cl. ........................ 203/43; 203/73; 203/80; 203/DIG. 25; 568/697; 568/699
[58] Field of Search ............... 203/80, 14, 43, 73, 203/DIG. 25, 46; 568/697, 699

[56] References Cited

U.S. PATENT DOCUMENTS

| | | | |
|---|---|---|---|
| 3,955,939 | 5/1976 | Sommer et al. | 203/71 |
| 3,989,762 | 11/1976 | Ester | 203/99 |
| 4,182,914 | 1/1980 | Imaizumi | 568/697 |
| 4,302,298 | 11/1981 | Mikitenko et al. | 203/75 |
| 4,334,964 | 6/1982 | Prezelj et al. | 203/85 |
| 4,393,250 | 7/1983 | Gottlieb et al. | 5568/697 |
| 4,463,999 | 9/1983 | Bezman | 44/56 |
| 4,544,776 | 10/1985 | Osterburg et al. | 203/43 |
| 4,603,225 | 7/1986 | Colaianne et al. | 585/331 |
| 4,666,563 | 5/1987 | Berg et al. | 203/14 |
| 4,857,664 | 8/1989 | Huang et al. | 568/695 |

FOREIGN PATENT DOCUMENTS 323138 12/1988 European Pat. Off. .
2078122 1/1982 United Kingdom ............ 203/43

Primary Examiner—Virginia Manoharan
Attorney, Agent, or Firm—Alexander J. McKillop; Charles J. Speciale; L. G. Wise

[57] ABSTRACT

In the diisopropyl ether production process, the distallation step for the separation of aqueous IPA recovered from the DIPE extraction operations is modified to avoid carrying out the distillation under conditions that yield IPA-water azeotrope providing lower overall process cost. The determination has been made that the overhead and bottom streams form an aqueous IPA fractionation process operated under off-azeotrope conditions in DIPE production can be recycled, respectively, to the DIPE reactor and extractor operations. Recycling the water and IPA overhead mixture eliminates the requirement for adding fresh water to the DIPE reactor. Returning the water and IPA bottom stream to the extractor reduces the requirement for distilled water addition to the extraction step. As a consequence, a less complex and costly aqueous IPA separation process is implemented.

13 Claims, 1 Drawing Sheet

DIPE PROCESS DESIGN

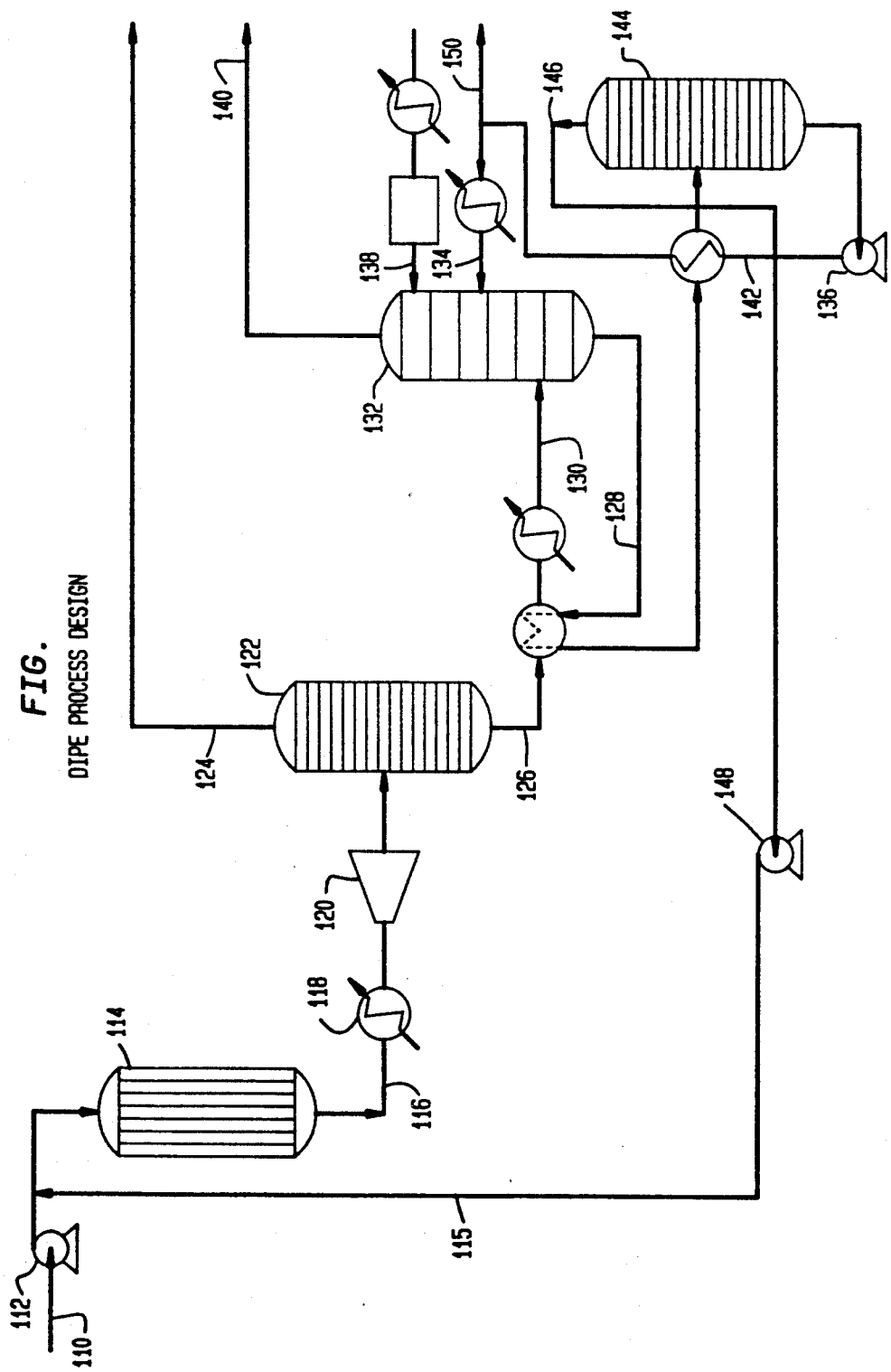
FIG.
DIPE PROCESS DESIGN

ADVANCES IN PRODUCT SEPARATION IN DIPE PROCESS

This invention relates to processes for the production of diisopropyl ether. The invention incorporates novel improvements in the product recovery operations for DIPE that enhance product separation while advantageously influencing overall etherification reaction operating conditions.

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels.

The catalytic hydration of olefins, particularly $C_3$ and $C_4$ olefins, to provide alcohols and ethers is a well-established art and is of significant commercial importance. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

The production of ether from secondary alcohols such as isopropanol and light olefins is known. As disclosed in U.S. Pat. No. 4,182,914, DIPE is produced from IPA and propylene in a series of operations employing a strongly acidic cation exchange resin as catalyst. Recently, processes for the hydration of olefins to provide alcohols and ethers using zeolite catalyst have been disclosed by Bell et al. in U.S. patent applications Ser. Nos. 414,630 filed Sept. 26, 1989; 427,926 filed Oct. 25, 1989; and U.S. Pat. Nos. 4,214,107 and 4,499,313 to Bell et al.; and U.S. Pat. No. 4,757,664 and 4,906,187 to T. Huang. These applications and patents are incorporated herein in their entirety by reference.

In the conversion of a water feedstream and a $C_3$ hydrocarbons feedstream comprising propene and propane to DIPE and IPA as conventionally practiced, the conversion per pass is about 60%. The reaction effluent is a mixture containing unreacted water, $C_3$ hydrocarbons and hydrocarbon oligomeric by-products, in addition to the DIPE and IPA products. Separating these components requires multiple distillation and extraction operations that represent a substantial part of the overall process costs. $C_3$ and any lower hydrocarbons present are effectively removed by distillation. However, separation of DIPE and IPA is accomplished by an aqueous extraction operation that requires a further distillation step to separate alcohol and water. This extraction and distillation of IPA from the reaction effluent in order to recycle IPA to the etherification reactor as typically carried out imposes an inordinate cost burden on the process in view of the formation of an IPA-water azeotrope which affects the complexity of the distillation tower design and operation.

It is an object of the present invention to provide a process for the production of diisopropyl ether at lower overall process cost and complexity.

It is another object of the present invention to provide an improved process for the steps of product separation and recycle of IPA in downstream DIPE operations.

Another object of the present invention is to utilize the DIPE water feed as at least a portion of the water used to wash the DIPE reactor effluent.

A further object of the invention is to provide an improved distillation step in the separation of aqueous isopropanol in the DIPE process.

SUMMARY OF THE INVENTION

It has been discovered that the DIPE process and distillation step for the separation of aqueous IPA recovered from the DIPE extraction operations can be modified to avoid carrying out the distillation under conditions that yield IPA-water azeotrope and that such modifications beneficially affect overall process cost. The determination has been made that the overhead and bottom streams from an aqueous IPA fractination process operated under off-azeotrope conditions in DIPE production can be recycled, respectively, to the DIPE reactor and extractor operations. Recycling the water and IPA overhead mixture eliminates the requirement for adding fresh water to the DIPE reactor while returning the water and IPA bottom stream to the extractor reduces the requirement for distilled or treated water addition to the extraction step. As a consequence of these unforeseeable process advantages, a less complex and less costly aqueous IPA fractionation process can be implemented.

More particularly, a process for the production of diisopropyl ether has been discovered which comprises the following steps: contacting $C_3$ hydrocarbon feedstock containing propene and recycle stream from isopropanol separator overhead, said recycle stream comprising a non-azeotropic mixture of water and isopropanol, with acidic olefin hydration and etherification catalyst under etherification conditions at elevated pressure to produce an effluent stream containing diisopropyl ether, isopropanol, unreacted water, unreacted $C_3$ hydrocarbons and higher olefinic hydrocarbons; separating the effluent stream at reduced pressure to produce a separator overhead stream comprising $C_3$- hydrocarbons and a bottom stream containing diisopropyl ether, isopropanol, unreacted water and higher olefinic hydrocarbons; extracting the bottom stream and the water reactant feed, or fresh water make-up to the process, from separation of the reactor effluent stream in contact with a portion of aqueous bottom stream from the isopropanol separator to produce an extractor aqueous phase enriched in isopropanol and an organic phase comprising said diisopropyl ether and higher hydrocarbons; separating the extractor aqueous phase to provide an overhead stream comprising the non-azeotropic water and IPA recycle stream and the aqueous bottom stream which is recycled to the extraction operation.

Relative to known DIPE technology, in the process for the production of diisopropyl ether comprising the steps of reacting a feedstream comprising propene with a water feedstream under hydration and etherification conditions in contact with acidic catalyst; separating the reaction effluent by distillation to provide a bottom stream containing diisopropyl ether, unreacted water, and isopropanol; extracting the bottom stream with water; and distilling the aqueous extract phase to separate isopropanol and water; the invention comprises an improvement comprising: reacting said propene with a water and isopropanol stream comprising a recycle of the overhead stream from distillation of said aqueous extract; and extracting said bottom stream with aqueous extract distillation bottom stream.

BRIEF DESCRIPTION OF THE DRAWING

The FIGURE is a process flow diagram of the process of the instant invention.

DETAIL DESCRIPTION OF THE INVENTION

In the process to prepare DIPE a feedstock comprising propene or a refinery $C_3$ hydrocarbon stream comprising olefins and paraffins, i.e., propene and propane, is contacted at elevated pressure with an acidic catalyst and water as a reactant to hydrate propene to form isopropanol (IPA) and etherify IPA to DIPE. Minor amounts of addition products of propene are also formed in the acidic catalyst environment, particularly hexenes and nonenes. On a per pass basis, the conversion of propene generally is about 60%, or between 50% and 70%. The effluent from the hydration and etherification zone is conventionally passed to a fractionator wherein a bottom stream is separated containing IPA and DIPE and an overhead stream that contains the unreacted $C_3$ hydrocarbons comprising propene and propane, if an olefin and paraffin feedstock has been used. The $C_3$ stream, typically containing both propene and propane, can be recompressed and recycled to the pressurized DIPE reactor. Since the recycle stream is rich in propane the DIPE feedstock stream pressure is increased in order to maintain the partial pressure of propene in the reactor. To avoid this, the recycle stream may be fractionated to purify propene recycle. Conventionally, DIPE is recovered by distillation and/or extraction of the fractionator bottom stream. This recovery system also separates an IPA stream and a water stream. The IPA stream is recycled to the etherification zone.

The operating conditions of the olefin hydration and etherification process are not especially critical and include a temperature of from about 60° to 450° C., preferably from about 90° to about 220° C. and most preferably from about 120° to about 200° C., a pressure of from about 100 (700 kPa) to about 3500 psi (24,500 kPa), preferably from about 500 (3500 kPa) to about 2000 psi (14,000 kPa), a water to olefin mole ratio of from about 0.1 to about 30, preferably from about 0.2 to about 15 and most preferably from about 0.3 to about 3.

The olefin hydration process can be carried out under dense phase, liquid phase, vapor phase or mixed vapor-liquid phase conditions in batch or continuous manner, preferably using a fixed bed reactor. A liquid hourly space velocity (LHSV) of from about 0.1 to about 20, preferably about 0.1–2, when operating continuously is suitable.

The catalyst employed in the olefin hydration and etherification operations is acidic resin catalyst such as sulfonated polystyrene. Also, shape-selective acidic zeolite catalyst can be used. In general, the useful catalysts include zeolites Y, Beta, ZSM-35 and MCM-22. MCM-22 is described in allowed U.S. patent application Ser. No. 456,702, filed Dec. 26, 1989 to Bell, et al., incorporated herein by reference. Preferred catalysts include Zeolite Beta, Zeolite Y and ZSM-35.

ZSM-35 is more particularly described in U.S. Pat. No. 4,016,245, the entire contents of which are incorporated herein by reference.

Zeolite Beta is described in U.S. Reissue Pat. No. 28,341 (of original U.S. Pat. No. 3,308,069), to which reference is made for details of this catalyst.

Zeolite Y is described in U.S. Pat. No. 3,130,007, to which reference is made for details of this catalyst.

The following Example describes the process of the present invention, including a description of the process as depicted in the FIGURE and a material balance for the process as tabulated in Table 1. Particular attention is directed to the novelty residing in the downstream separation of the products of the hydration and etherification reaction and, more particularly, to the operation of the IPA-water fractionator with recycle streams provided to the extractor and reactor section.

EXAMPLE

Referring to the FIGURE and to Table 1, a feed 110 containing about 157 parts of propene per 100 parts of propane is washed with water to remove basic nitrogen contaminants and pumped 112 to a DIPE reactor 114 at a pressure of about 1500 psig (10,500 kPa) and 320° F. (160° C.) in combination with an isopropanol/water recycle stream 115. Typically, the feedstream comprises FCC propane/propene and is fed to parallel DIPE tubular reactors. The propene reacts with water to produce DIPE at a conversion of about 57%. The reaction products exit the reactor as an effluent 116 at a temperature of about 340° F. (171° C.) and are cooled 118 to about 150° F. (66° C.). The effluent contains about 100 parts of DIPE and 63 parts of IPA per 100 parts of propane feed as shown in Table 1. The cool effluent is passed through an expander 120 to reduce the pressure to about 250 psig (121 kPa) and a temperature of about 174° F. (79° C.). Next, the

TABLE 1

| | MATERIAL BALANCE FLOW RATE (parts/100 parts $C_3$ feed) | | | | | | | | | |
|---|---|---|---|---|---|---|---|---|---|---|
| | COMPONENT | | | | | | | | | |
| OPERATION | $C_2$ | $C_2=$ | $C_3$ | $C_3=$ | $C_4s$ | IPA | DIPE | $C_5=+$ | $H_2O$ | Total |
| FEED | 0.38 | 1.10 | 100.00 | 157.32 | 3.26 | | | | | 262.06 |
| IPA RECYCLE | | | | | | 62.92 | .31 | | 31.46 | 94.69 |
| REACTOR EFFLUENT | 0.38 | 1.10 | 100.00 | 67.63 | 1.58 | 63.07 | 100.18 | 10.54 | 12.27 | 356.75 |
| SPLITTER OVERHEAD | 0.38 | 1.10 | 100.00 | 67.63 | 1.11 | .03 | .12 | | .01 | 170.38 |
| SPLITTER BOTTOMS | | | | | .47 | 63.04 | 100.07 | 10.54 | 12.26 | 186.37 |
| EXTRACTOR ETHER PHASE | | | | | .47 | .11 | 99.75 | 10.54 | 1.12 | 111.99 |
| EXTRACTOR AQUEOUS | | | | | | 62.98 | .32 | | 753.27 | 816.56 |
| IPA COLUMN OVERHEAD | | | | | | 62.92 | .32 | | 31.46 | 94.70 |
| IPA COLUMN BOTTOMS | | | | | | | .05 | | 721.81 | 721.86 | effluent is passed to a 15-tray propane/propene splitter 122 and $C_3$ and lighter material are removed as an overhead stream 124 at a temperature of about 100° F. (38° C.). The splitter bottoms stream 126, exiting the splitter at a temperature of about 275° F. (135° C.) and a pressure of 60 psig (420 kPa), is let down in pressure in a valve and cooled to about 100° F. (38° C.) by exchanging heat against an extractor bottoms stream 128 and cooling water. The cooled stream 130 is then fed to an extractor 132 which operates at a pressure of 40 psig (280 kPa) and a water:feed volume ratio of 3:1. Water is fed to the extractor as a recycle stream 134 from the IPA column following pumping 136 and heat exchange to provide a recycle inlet stream temperature to the extractor of about 100° F. (38° C.) A make-up boiler feed water stream 138 is also added to the extractor to compensate for any water losses. The ether phase contains 89% DIPE, 9.4% $C_5=+$, 1% water and traces of $C_4s$ and IPA. This stream is removed from the extractor overhead 140 at a temperature of about 100° F. (38° C.) and 40 psig (280 kPa). The aqueous extractor bottom stream 128 is preheated in succession to about 180° F. (82° C.) against splitter bottoms as previously noted and IPA column bottoms 142 before being fed to the IPA column 144. The IPA column is a 15-tray column which operates at a pressure of about 10 psig (70 KPa). The overhead stream 146 from the column is recycled back to the reactor through pump 148 at a temperature of about 100° F. (38° C.) and 1600 psig (11,200 kPa) to provide stream 115 at the required IPA weight hourly space velocity (WHSV) of 0.10 and water WHSV of 0.05. The IPA column bottoms stream at a temperature of about 117° C. is recycled to the extractor after a small slip stream 150 is taken to maintain high purity.

The preferred catalyst in the instant Example is zeolite Beta.

Examination of Table 1 shows that the composition of the recycle overhead stream from the IPA column contains an amount of water considerably above that contained in IPA-water azeotrope. Consequently, the complexity of the fractionator design is simpler than that conventionally used in DIPE production where the IPA column is designed and operated to produce an overhead containing a minimal amount of water. The discovery of the utility of the water rich IPA overhead stream and IPA rich aqueous bottom stream as described herein before permits the design and operation of a such simpler and less costly IPA column.

While the instant invention has been described by specific examples and embodiments, there is no intent to limit the inventive concept except as set forth in the following claims.

What is claimed is:

1. A process for production of diisopropyl ether comprising;
    a) contacting $C_3$ hydrocarbon feedstock containing propene and an aqueous feedstream comprising a recycle stream from isopropanol fractionator overhead, with acidic olefin hydration and etherification catalyst under etherification conditions at elevated pressure to produce an effluent stream containing diisopropyl ether, isopropanol, unreacted water, unreacted $C_3$ hydrocarbons and higher olefinic hydrocarbons;
    b) distilling said effluent stream at reduced pressure to produce an overhead stream comprising $C_3$- hydrocarbons and a bottom stream containing diisopropyl ether, isopropanol, water and higher olefinic hydrocarbons;
    c) extracting step (b) bottom stream with water and/or a portion of aqueous bottom stream from said isopropanol fractionator to produce an extractor aqueous phase containing isopropanol and an organic phase comprising said diisopropyl ether and higher olefinic hydrocarbons;
    d) distilling said extractor aqueous phase to provide step (a) recycle stream consisting essentially of a non-azetropic mixture of water and isopropanol and step (c) portion of aqueous bottom stream, wherein the ratio of water to isopropanol in said recycle stream is greater than the ratio of water to isopropanol in a water-isopropanol azeotrope.

2. The process of claim 1 wherein the amount of water in step (a) recycle stream is sufficient to accomplish the hydration of said propene.

3. The process of claim 2 wherein said recycle stream consists essentially of isopropanol weight hourly space velocity of about 0.10 and water WHSV of about 0.05.

4. The process of claim 1 wherein step (d) distillation is carried out to provide an overhead stream temperature of about 38° C. at about 70 kPa and a bottom stream temperature of about 117° C.

5. The process of claim 1 wherein step (b) bottom stream is cooled before extracting.

6. The process of claim 1 wherein said acidic hydration and etherification catalyst is selected from the group consisting of ZSM-5, zeolite Beta and acidic resins.

7. The process of claim 1 wherein said etherification conditions comprise temperature of about 160° C. and pressure of about 10,500 kPa.

8. In a process for the production of diisopropyl ether comprising the steps of reacting a feedstream comprising propene with a water feedstream under hydration and etherification conditions in contact with acidic catalyst; separating a reaction effluent by distillation to provide a bottom stream containing diisopropyl ether and isopropanol; extracting the bottom stream with water; and distilling an aqueous extract phase to separate isopropanol and water; the improvement comprising: reacting said propene with a water and isopropanol stream consisting essentially of a non-azetropic recycle of the overhead stream from distillation of said aqueous extract, wherein the ratio of water to isopropanol in said recycle stream is greater than the ratio of water to isopropanol in a water-isopropanol azeotrope; and extracting said bottom stream with aqueous extract distillation bottom stream in addition to water.

9. The process of claim 8 wherein the amount of water in said recycle stream is sufficient to accomplish the hydration of said propene.

10. The process of claim 9 wherein said recycle stream consists essentially of isopropanol weight hourly space velocity of about 0.10 and water WHSV of about 0.05.

11. The process of claim 8 wherein said distillation of aqueous extract is carried out to provide an overhead stream temperature of about 38° C. at a pressure of about 70 kPa and a bottom stream temperature of about 117° C.

12. The process of claim 8 wherein said acidic hydration and etherification catalyst is selected from the group consisting of ZSM-5, zeolite Beta and acidic resins.

13. The process of claim 8 wherein said etherification conditions comprise temperature of about 160° C. and pressure of about 10,500 kPa.

* * * * *